US007176466B2

(12) United States Patent
Rousso et al.

(10) Patent No.: US 7,176,466 B2
(45) Date of Patent: Feb. 13, 2007

(54) MULTI-DIMENSIONAL IMAGE RECONSTRUCTION

(75) Inventors: Benny Rousso, Rishon LeZion (IL); Michael Nagler, Tel Aviv (IL)

(73) Assignee: Spectrum Dynamics LLC, Orangeburg, NY (US)

(*) Notice: Subject to any disclaimer, the term of this patent is extended or adjusted under 35 U.S.C. 154(b) by 0 days.

(21) Appl. No.: 11/034,007

(22) Filed: Jan. 13, 2005

(65) Prior Publication Data

US 2005/0205792 A1 Sep. 22, 2005

Related U.S. Application Data

(60) Provisional application No. 60/535,830, filed on Jan. 13, 2004.

(51) Int. Cl.
*G01T 1/161* (2006.01)

(52) U.S. Cl. .......................... 250/370.08; 250/363.02

(58) Field of Classification Search .......... 250/370.08, 250/363.02, 363.1
See application file for complete search history.

(56) References Cited

U.S. PATENT DOCUMENTS

| | | | | |
|---|---|---|---|---|
| 2,776,377 | A | | 1/1957 | Anger |
| 3,340,866 | A | | 9/1967 | Nöller |
| 3,684,887 | A | | 8/1972 | Hugonin |
| 3,719,183 | A | | 3/1973 | Schwartz |
| 3,739,279 | A | | 6/1973 | Hollis |
| 3,971,362 | A | | 7/1976 | Pope et al. |
| 4,278,077 | A | | 7/1981 | Mizumoto |
| 4,364,377 | A | | 12/1982 | Smith |
| 4,521,688 | A | * | 6/1985 | Yin ...................... 250/363.04 |
| 4,674,107 | A | | 6/1987 | Urban et al. |
| 4,689,041 | A | | 8/1987 | Corday et al. |
| 4,689,621 | A | | 8/1987 | Kleinberg |
| 4,773,430 | A | | 9/1988 | Porath |
| 4,828,841 | A | | 5/1989 | Porter et al. |
| 4,844,067 | A | | 7/1989 | Ikada et al. |
| 4,844,076 | A | | 7/1989 | Lesho et al. |
| 4,893,013 | A | | 1/1990 | Denen et al. |
| 4,928,250 | A | | 5/1990 | Greenberg et al. |

(Continued)

FOREIGN PATENT DOCUMENTS

WO WO 92/00402 9/1992

(Continued)

OTHER PUBLICATIONS

Pardridge et al. "Tracer Kinetic Model of Blood-Brain Barrier Transport of Plasma Protein-Bound Ligands", Journal of Clinical Investigation, 74: 745-752, 1984.

(Continued)

*Primary Examiner*—Otilia Gabor

(57) ABSTRACT

Apparatus for radiation based imaging of a non-homogenous target area having distinguishable regions therein, comprises: an imaging unit configured to obtain radiation intensity data from a target region in the spatial dimensions and at least one other dimension, and an image four-dimension analysis unit analyzes the intensity data in the spatial dimension and said at least one other dimension in order to map the distinguishable regions. The system typically detects rates of change over time in signals from radiopharmaceuticals and uses the rates of change to identify the tissues. In a preferred embodiment, two or more radiopharmaceuticals are used, the results of one being used as a constraint on the other.

52 Claims, 10 Drawing Sheets

U.S. PATENT DOCUMENTS

| | | | | |
|---|---|---|---|---|
| 4,929,832 | A | 5/1990 | Ledley | |
| 4,959,547 | A | 9/1990 | Carroll et al. | |
| 5,014,708 | A | 5/1991 | Hayashi et al. | |
| 5,032,729 | A | 7/1991 | Charpak | |
| 5,033,998 | A | 7/1991 | Corday et al. | |
| 5,070,878 | A | 12/1991 | Denen | |
| 5,119,818 | A | 6/1992 | Carroll et al. | |
| 5,151,598 | A | 9/1992 | Denen | |
| 5,170,055 | A | 12/1992 | Carroll et al. | |
| 5,170,789 | A | 12/1992 | Narayan et al. | |
| 5,243,988 | A | 9/1993 | Sieben et al. | |
| 5,246,005 | A | 9/1993 | Carroll et al. | |
| 5,249,124 | A | 9/1993 | DeVito | |
| 5,279,607 | A | 1/1994 | Schentag et al. | |
| 5,299,253 | A | 3/1994 | Wessels | |
| 5,307,808 | A | 5/1994 | Dumoulin et al. | |
| 5,383,456 | A | 1/1995 | Arnold et al. | |
| 5,395,366 | A | 3/1995 | D'Andrea | |
| 5,399,868 | A | 3/1995 | Jones et al. | |
| 5,415,181 | A | 5/1995 | Hogrefe et al. | |
| 5,441,050 | A | 8/1995 | Thurston et al. | |
| 5,448,073 | A | 9/1995 | Jeanguillaume | |
| 5,475,219 | A | 12/1995 | Olson | |
| 5,484,384 | A | 1/1996 | Fearnot | |
| 5,489,782 | A * | 2/1996 | Wernikoff | 250/369 |
| 5,493,595 | A | 2/1996 | Schoolman | |
| 5,604,531 | A | 2/1997 | Iddan et al. | |
| 5,617,858 | A | 4/1997 | Taverna et al. | |
| 5,635,717 | A | 6/1997 | Popescu | |
| 5,657,759 | A | 8/1997 | Essen-Moller | |
| 5,682,888 | A | 11/1997 | Olson et al. | |
| 5,690,691 | A | 11/1997 | Chen et al. | |
| 5,694,933 | A * | 12/1997 | Madden et al. | 600/431 |
| 5,716,595 | A | 2/1998 | Goldenberg | |
| 5,727,554 | A | 3/1998 | Kalend et al. | |
| 5,729,129 | A | 3/1998 | Acker | |
| 5,732,704 | A | 3/1998 | Thurston et al. | |
| 5,744,805 | A | 4/1998 | Raylman et al. | |
| 5,833,603 | A | 11/1998 | Kovacs et al. | |
| 5,842,977 | A | 12/1998 | Lesho et al. | |
| 5,846,513 | A | 12/1998 | Carroll et al. | |
| 5,857,463 | A | 1/1999 | Thurston et al. | |
| 5,871,013 | A | 2/1999 | Wainer et al. | |
| 5,880,475 | A | 3/1999 | Oka et al. | |
| 5,900,533 | A | 5/1999 | Chou | |
| 5,916,167 | A | 6/1999 | Kramer et al. | |
| 5,928,150 | A | 7/1999 | Call | |
| 5,932,879 | A | 8/1999 | Raylman et al. | |
| 5,939,724 | A | 8/1999 | Eisen et al. | |
| 5,984,860 | A | 11/1999 | Shan | |
| 5,987,350 | A | 11/1999 | Thurston | |
| 5,993,378 | A | 11/1999 | Lemelson | |
| 6,002,480 | A | 12/1999 | Izatt et al. | |
| 6,082,366 | A | 7/2000 | Andra et al. | |
| 6,107,102 | A | 8/2000 | Ferrari | |
| 6,115,635 | A | 9/2000 | Bourgeois | |
| 6,132,372 | A | 10/2000 | Essen-Moller | |
| 6,135,955 | A * | 10/2000 | Madden et al. | 600/436 |
| 6,173,201 | B1 | 1/2001 | Front | |
| 6,205,347 | B1 | 3/2001 | Morgan et al. | |
| 6,212,423 | B1 | 4/2001 | Krakovitz | |
| 6,240,312 | B1 | 5/2001 | Alfano et al. | |
| 6,242,743 | B1 | 6/2001 | DeVito et al. | |
| 6,261,562 | B1 | 7/2001 | Xu et al. | |
| 6,263,229 | B1 | 7/2001 | Atalar et al. | |
| 6,271,524 | B1 | 8/2001 | Wainer et al. | |
| 6,271,525 | B1 | 8/2001 | Majewski et al. | |
| 6,280,704 | B1 | 8/2001 | Schutt et al. | |
| 6,324,418 | B1 | 11/2001 | Crowley et al. | |
| 6,346,706 | B1 | 2/2002 | Rogers et al. | |
| 6,368,331 | B1 | 4/2002 | Front et al. | |
| 6,407,391 | B1 * | 6/2002 | Mastrippolito et al. | 250/363.1 |
| 6,426,917 | B1 | 7/2002 | Tabanou et al. | |
| 6,429,431 | B1 | 8/2002 | Wilk | |
| 6,431,175 | B1 | 8/2002 | Penner et al. | |
| 6,453,199 | B1 | 9/2002 | Kobozev | |
| 6,516,213 | B1 | 2/2003 | Nevo | |
| 6,525,320 | B1 | 2/2003 | Juni | |
| 6,525,321 | B2 | 2/2003 | Juni | |
| 6,560,354 | B1 | 5/2003 | Maurer et al. | |
| 6,567,687 | B2 | 5/2003 | Front et al. | |
| 6,584,348 | B2 | 6/2003 | Glukhovsky | |
| 6,587,710 | B1 | 7/2003 | Wainer | |
| 6,592,520 | B1 | 7/2003 | Peszynski et al. | |
| 6,607,301 | B1 | 8/2003 | Glukhovsky et al. | |
| 6,611,141 | B1 | 8/2003 | Schulz et al. | |
| 6,614,453 | B1 | 9/2003 | Suri et al. | |
| 6,628,983 | B1 | 9/2003 | Gagnon | |
| 6,628,984 | B2 * | 9/2003 | Weinberg | 600/436 |
| 6,662,036 | B2 | 12/2003 | Cosman | |
| 6,748,259 | B1 * | 6/2004 | Benaron et al. | 600/476 |
| 2002/0072784 | A1 | 6/2002 | Sheppard, Jr. et al. | |
| 2002/0085748 | A1 | 7/2002 | Baumberg | |
| 2003/0001837 | A1 | 1/2003 | Baumberg | |
| 2003/0013966 | A1 | 1/2003 | Barnes et al. | |
| 2003/0063787 | A1 | 4/2003 | Natanzon et al. | |
| 2003/0191430 | A1 | 10/2003 | D'Andrea et al. | |
| 2003/0208117 | A1 | 11/2003 | Shwartz et al. | |
| 2004/0015075 | A1 | 1/2004 | Kimchy et al. | |
| 2004/0054248 | A1 | 3/2004 | Kimchy et al. | |
| 2004/0054278 | A1 | 3/2004 | Kimchy et al. | |
| 2004/0116807 | A1 | 6/2004 | Amrami et al. | |

FOREIGN PATENT DOCUMENTS

| | | |
|---|---|---|
| WO | WO 99/03003 | 1/1999 |
| WO | WO 00/31522 | 2/2000 |
| WO | WO 00/18294 | 6/2000 |
| WO | WO 02/058531 | 1/2002 |
| WO | WO 02/16965 | 2/2002 |
| WO | WO 2004/042546 | 5/2004 |

OTHER PUBLICATIONS

Reutter et al. "Direct Least Squares Estimation of Spatiotemporal Distributions From Dynamic SPECT Projections Using A Spatial Segmentation and Temporal B-Splines", IEEE Transactions on Medical Imaging, 19(5): 434-450, 2000.

Huesman et al. "Kinetic Parameter Estimation From SPECT Cone-Beam Projection Measurements", Physics in Medicine and Biology, 43(4): 973-982, 1998.

Reutter et al. "Kinetic Parameter Estimation From Attenuated SPECT Projection Measurements", IEEE Transactions on Nuclear Science, 45(6): 3007-3013, 1998.

Garcia et al. "Accuracy of Dynamic SPECT Acquisition for Tc-99m Teboroxime Myocardial Perfusion Imaging: Preliminary Results", American College of Cardiology, 51st Annual Scientific Session, Atlanta, Georgia, USA, 8 P., 2002.

Jeanguillaume et al. "From the Whole-Body Counting to Imaging: The Computer Aided Collimation Gamma Camera Project (CACAO)", Radiation Projection Dosimetry 89(3-4): 349-352, 2000.

Quartuccia et al. "Computer Assisted Collimation Gama Camera: A New Approach to Imaging Contaminated Tissues", Radiation Projection Dosimetry, 89(3-4): 343-348, 2000.

Piperno et al. "Breast Cancer Screening by Impedance Measurements", Frontiers Med. Biol. Engng., 2(2): 11-17, 1990.

Rajshekhar "Continuous Impedence Monitoring During CT-Guided Stereotactic Surgery: Relative Value in Cystic and Solid Lesions", British Journal of Neurosurgery, 6: 439-444, 1992.

Jessup "Tumor Markers—Prognostic and Therapeutic Implications for Colorectal Carcinoma", Surgical Oncology, 7: 139-151, 1998.

Corstens et al. "Nuclear Medicine's Role in Infection and Inflammation", The Lancet, 354: 765-770, 1999.

Mori et al. "Overexpression of Matrix Metalloproteinase-7mRNA in Human Colon Carcinomas", Cancer, 75: 1516-1519, 1995.

Erbil et al. "Use and Limitations of Serum Total and Lipid-Bound Sialic Acid Concentrations as Markers for Colorectal Cancer", Cancer, 55: 404-409, 1985.

Molinolo et al. "Enhanced Tumor Binding Using Immunohistochemical Analyses by Second Generation Anti-Tumor-Associated Glycoprotein 72 Monoclonal Antibodies versus Monoclonal Antibody B72.3 in Human Tissue", Cancer Research, 50: 1291-1298, 1990.

Day et al. "Localization of Radioiodinated Rat Fibrogen in Transplanted Rat Tumors", Journal of the National Cancer Institute, 23(4): 799-812, 1959.

Garcia et al. "Accuracy of Dynamic SPECT Acquisition for Tc-99m Teboroxime Myocardial Perfusion Imaging: Preliminary Results", American College of Cardiology 51st Annual Scientific Session, Atlanta, Georgia, USA, p. 1-8, 2002.

Bromiley et al. "Attenuation Correction in PET Using Consistency Conditions and A Three-Dimensional Template", IEEE Transactions on Nuclear Science, 48(4): 1371-1377, 2001. p. 1376, col. 2, § 2.

Hayakawa et al. "A PET-MRI Registration Technique for PET Studies of the Rat Brain", Nuclear Medicine & Biology, 27: 121-125, 2000. p. 121, col. 1.

Lavallée et al. "Building A Hybrid Patient's Model for Augmented Reality in Surgery: A Registration Problem", Computing in Biological Medicine, 25(2): 149-164, 1995. p. 149-150.

Kojima et al. "Quantitative Planar Imaging Method for Measurement of Renal Activity by Using A Conjugate-Emission Image and Transmission Data", Medical Physics, 27(3): 608-615, 2000. p. 608.

* cited by examiner

MULTI-DIMENSIONAL IMAGE RECONSTRUCTION

RELATIONSHIP TO EXISTING APPLICATIONS

The present application claims priority from U.S. Provisional Patent Application No. 60/535,830 filed Jan. 13, 2004, the contents of which are hereby incorporated by reference.

FIELD AND BACKGROUND OF THE INVENTION

The present invention relates to multi-dimensional image reconstruction and, more particularly, but not exclusively to such image reconstruction based on a diffuse radioactive source or sources.

Radiological imaging is generally carried out on a living target, which of course means a mix of tissues in close proximity, if not actually overlapping. The general procedure is to feed the patient with one or more radioactive markers prior to the imaging process. The radioactive markers are taken up by the digestive system and pass into the bloodstream. From the bloodstream the marker passes into the different tissues at varying rates depending on the tissue type. Some tissues absorb markers faster than others and some tissues absorb certain markers faster than others. Furthermore certain tissues flush out the markers faster than others, and again the rate of flushing out may also depend on the kind of marker being used.

As a result, radioactive marking in fact creates a dynamic system in the body in which the relative darkness of a given tissue is related to a time factor. The radiologist knows that if he wants a good image of say the liver following application of a given marker then he should wait a certain number of hours from application of the marker before taking the image. Even so, the liver is not differentiated clearly from the other tissues.

Examples of radiopharmaceuticals include monoclonal antibodies or other agents, e.g., fibrinogen or fluorodeoxyglucose, tagged with a radioactive isotope, e.g., Technitium-99m, Gallium-67, Thallium-201, Indium-111, Iodine-123, Iodine-125 and Fluorine-18, which may be administered orally or intravenously. The radiopharmaceuticals are designed to concentrate in the area of a tumor, and the uptake of such radiopharmaceuticals in the active part of a tumor, or other pathologies such as an inflammation, is higher and more rapid than in the tissue that neighbors the tumor. Thereafter, a radiation-emission-measuring-probe, which may be configured for extracorporeal or intracorporeal use, is employed for locating the position of the active area. Another application is the detection of blood clots with radiopharmaceuticals such as ACUTECT from Nycomed Amersham for the detection of newly formed thrombosis in veins, or clots in arteries of the heart or brain, in an emergency or operating room. Yet other applications include radioimaging of myocardial infarct using agents such as radioactive anti-myosin antibodies, radioimaging specific cell types using radioactively tagged molecules (also known as molecular imaging), etc.

The usual preferred emission for such applications is that of gamma rays, which emission is in the energy range of approximately 11–511 KeV. Beta radiation and positrons may also be detected.

Radioactive-emission imaging is performed with a radioactive-emission-measuring detector, such as a room temperature, solid-state CdZnTe (CZT) detector, which is among the more promising that is currently available. It may be configured as a single-pixel or a multi-pixel detector, and may be obtained, for example, from eV Products, a division of II–VI Corporation, Saxonburg Pa., 16056, or from IMARAD IMAGING SYSTEMS LTD., of Rehovot, ISRAEL, 76124, www.imarad.com, or from another source. Alternatively, another solid-state detector such as CdTe, HgI, Si, Ge, or the like, or a combination of a scintillation detector (such as NaI(TI), LSO, GSO, CsI, CaF, or the like) and a photomultiplier, or another detector as known, may be used.

Considering the issue in greater detail, certain biological or chemical substances such as targeted peptides, monoclonal antibodies and others, are used for tagging specific living molecules for diagnostic purposes. Ideally, these antibodies are specific to the desired type of cells, based on adhering only to specific molecular structures in which the antigene matching the antibody is highly expressed. The use of imaging devices such as a nuclear gamma probe or a visual video probe can detect radiation emanating from taggants such as radionuclei or fluorescent dies that have been appended to the antibody before being delivered to the living body. An example is a cancerous cell of a prostate tumor on whose membrane there is an over expression of the Prostate Specific Membrane Antigen (PSMA). When a monoclonal antibody (Mab) such as Capromab Pendetide (commercially available as ProstaScint manufactured by Cytogen Corp.) is labeled with radioactive Indium (In 111) and is systemically delivered to the body, the Mab is carried by the blood stream and upon reaching the prostate tissue, adheres to the PSMA. The high energy radiation photons emitted by the radioactive Indium can be detected using a nuclear camera, indicating the presence and the specific location of the tumor.

Unfortunately, given the complexity of living organisms, in many instances the same antigen is also expressed in more than just the tissue under investigation. The antibody will thus also "paint" additional tissues such as infection areas, in addition to the tissue of interest. The radioactive readings taken from this additional tissue will be falsely interpreted as tumor areas, reducing the specificity of the test being performed.

The 'Target to Background' ratio that characterizes every such antibody for a given target cell type is one of the major issues that determine the ability to perform proper diagnosis, and guided procedures.

Since the uptake clearance of such a marker by the various tissues (target and background) varies over time, standard diagnosis protocols usually recommend taking an image at the time at which the ratio of Target emission vs. Background emission is the highest.

In an experimental system tried out by researchers, two markers were supplied to various patients and then images were taken at successive intervals for each of the markers. Certain features in the target areas showed up clearly in all images, other features were clear for all images of one marker but faded in and faded out for the other marker, and yet other features faded in and out for both markers but at different times. The researchers were able to use their knowledge of the behaviors of the two markers with different tissues in order to identify the features in the images.

The above system therefore relies on the knowledge of the researchers to put together information received from multiple images into an understanding of what the radio-imaging shows. In the general hospital environment it is not possible to guarantee that the necessary expertise is available, at least not for the amount of time that such a system would require.

There is thus a widely recognized need for, and it would be highly advantageous to have, a radiological imaging system devoid of the above limitations.

SUMMARY OF THE INVENTION

According to one aspect of the present invention there is provided apparatus for radiation based imaging of a non-homogenous target area having distinguishable regions therein, the apparatus comprising:

an imaging unit configured to obtain radiation intensity data from said target region in the spatial dimensions and at least one other dimension, and an image four-dimension analysis unit associated with said imaging unit for analyzing said obtained intensity data in said spatial dimension and said at least one other dimension in order to map said distinguishable regions. By image four-dimension analysis unit is meant a unit that is able to analyze image data based on the spatial dimensions plus one other dimension, such as time.

Preferably, said image four dimension analysis unit is configured to constrain image output to a subset of said mapped distinguishable regions.

Preferably, said image four-dimension analysis unit is configured to use said constraining to increase a resolution of said image output.

Preferably, the distinguishable regions have differential takeup characteristics over time for radioactive markers and said multi-dimensional data includes a time component, said image analysis unit being configured to compare changes in detected intensity over time with said takeup characteristics in order to carry out said mapping.

Preferably, at least two radioactive markers are applied to said target region, each of said markers having different takeup characteristics for respective ones of said regions, and each of said markers producing respectively distinguishable radiation, said image analysis unit being configured to use distinguishability of the radiation between said markers as an additional dimension in order to carry out said mapping.

Preferably, at least two radioactive markers are applied to said target region, each of said markers having different takeup characteristics for respective ones of said regions, and each of said markers producing respectively distinguishable radiation, said image analysis unit being configured to use distinguishability of the radiation between said markers as said at least one other dimension in order to carry out said mapping.

Preferably, said image analysis unit is configured to use said mapping to generate an image comprising said regions as distinct entities.

Preferably, said image analysis unit is configured to use said mapping to generate an image showing only a subset of said regions and to exclude at least one other of said regions.

Preferably, said regions at least partially overlap, said image analysis unit being configured to show radiation due to a subset of said regions and to exclude radiation from at least one other of said regions as noise.

Preferably, said image analysis unit is configured to use said mapping to generate an image comprising said regions as distinct entities.

Preferably, said image analysis unit is configured to use said mapping to generate an image showing only a subset of said regions and to exclude at least one other of said regions.

Preferably, said regions at least partially overlap, said image analysis unit being configured to show radiation due to a subset of said regions and to exclude radiation from at least one other of said regions as noise.

Preferably, said imaging unit comprises at least one directional Geiger counter.

Preferably, said imaging unit comprises a plurality of directional Geiger counters.

Preferably, said imaging unit comprises a controller for directing said Geiger counter to take images from a set of locations optimized to obtain three-dimensional spatial data for a given target.

Preferably, said non-homogenous target area is a region of living tissue, and said distinguishable regions are at least one of a group comprising: different tissues, different organs, blood and organ tissue, and tissue regions of differential pathologies.

Preferably, one of said radioactive markers is Thallium-201 and another of said radioactive markers is technetium 99.

Preferably, said image analysis unit is configured to ignore image data as being from outside said target area if said image data does not conform to at least one of said takeup characteristics.

The apparatus may be configured to use said mapping to identify at least one region of low emissivity, thereby to concentrate imaging resources on said identified region.

Preferably, said imaging is via voxels of said target area and wherein said concentrating imaging resources comprises merging voxels of said identified region.

Preferably, said concentrating resources comprises concentrating resources of said imaging unit on said identified region.

Preferably, said mapping comprises a first mapping to identify an organ and a second mapping constrained within said organ.

According to a second aspect of the present invention, there is provided a method for constraining image data obtained from a non-homogenous target area having a plurality of distinct regions using at least one radioactive marker, the method comprising:

obtaining radiation intensity data from said target area in the spatial dimensions and at least one other dimension, and analyzing said radiation intensity data using said dimensions in order to classify data pertaining to respective distinct regions and to produce an output constrained to a subset of said distinct regions.

Preferably, said at least one radioactive marker has a time absorption characteristic which is different for ones of said distinct regions and wherein said at least one other dimension is a time dimension.

Preferably, there are provided at least two radioactive markers, each having respectively different time absorption characteristics for each of said distinct regions, and wherein said at least one other dimension is a time dimension.

Preferably, there are provided at least two radioactive markers, each producing a distinct signal and each respectively having different time absorption characteristics for each of said distinct regions, and wherein said at least one other dimension is a dimension indicating individual markers.

Preferably, there are provided at least two radioactive markers, each producing a distinct signal and each respectively having different time absorption characteristics for each of said distinct regions, and wherein said at least one other dimension comprises a time dimension and a dimension indicating individual markers.

Preferably, said classifying identifies at least one region of low emissivity, the method further comprising concentrating imaging resources on said identified region.

Preferably, said imaging is via voxels of said target area and said concentrating imaging resources comprises merging voxels of said identified region.

Preferably, said concentrating resources comprises concentrating resources of said imaging unit on said identified region.

Preferably, said classifying comprises a first classification to identify an organ and a second classification constrained within said organ.

According to a third aspect of the present invention there is provided apparatus for radiation based imaging of a non-homogenous target area having distinguishable regions therein, the apparatus comprising:

an imaging unit configured to obtain radiation intensity data from said target region in the spatial dimensions and at least one other dimension, an image analysis unit associated with said imaging unit for analyzing said obtained intensity data in said spatial dimension and said at least one other dimension in order to map said distinguishable regions, and using said mapping to control use of imaging resources.

Unless otherwise defined, all technical and scientific terms used herein have the same meaning as commonly understood by one of ordinary skill in the art to which this invention belongs. The materials, methods, and examples provided herein are illustrative only and not intended to be limiting.

Implementation of the method and system of the present invention involves performing or completing certain selected tasks or steps manually, automatically, or a combination thereof. Moreover, according to actual instrumentation and equipment of preferred embodiments of the method and system of the present invention, several selected steps could be implemented by hardware or by software on any operating system of any firmware or a combination thereof. For example, as hardware, selected steps of the invention could be implemented as a chip or a circuit. As software, selected steps of the invention could be implemented as a plurality of software instructions being executed by a computer using any suitable operating system. In any case, selected steps of the method and system of the invention could be described as being performed by a data processor, such as a computing platform for executing a plurality of instructions.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in order to provide what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings.

DESCRIPTION OF THE PREFERRED EMBODIMENTS

Figure 1:
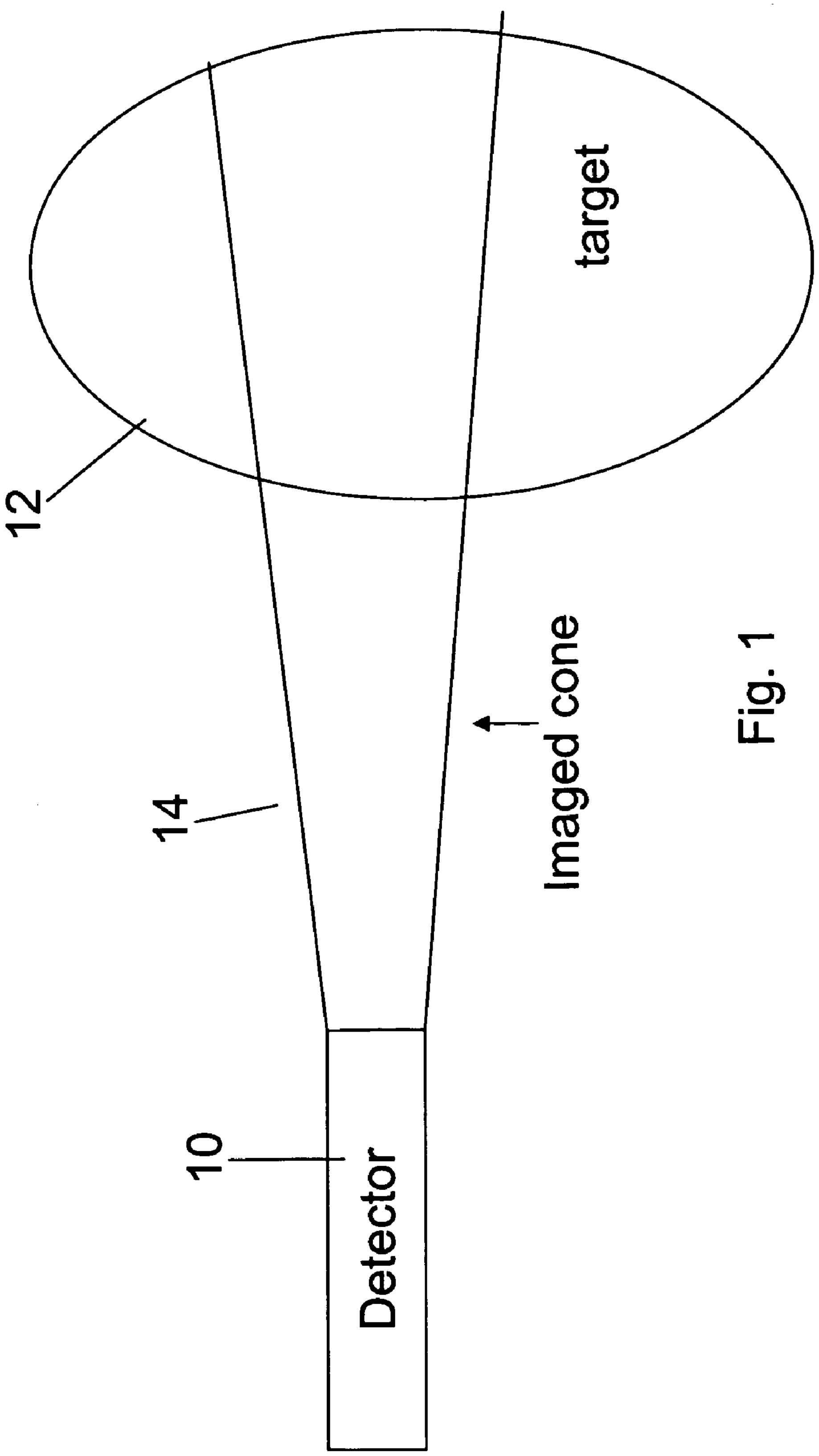
FIG. 1 is a simplified diagram showing a single detector detecting over a target region.

The present embodiments comprise an apparatus and a method for radiation based imaging of a non-homogenous target area having regions of different material or tissue type or pathology. The imaging uses multi-dimensional data of the target area in order to distinguish the different regions. Typically the multi-dimensional data involves time as one of the dimensions. A radioactive marker has particular time-absorption characteristics which are specific for the different tissues, and the imaging device is programmed to constrain its imaging to a particular characteristic.

The result is not merely an image which concentrates on the tissue of interest but also, because it is constrained to the tissue of interest, is able to concentrate imaging resources on that tissue and thus produce a higher resolution image than the prior art systems which are completely tissue blind.

The principles and operation of a radiological imaging system according to the present invention may be better understood with reference to the drawings and accompanying description.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

Reference is now made to FIG. 1, which illustrates a simple Geiger counter taking an image of a target according to the prior art. Geiger counter 10 is placed in association with target 12 and absorbs any radioactive particles that come its way. In general the radioactive particles arriving at the Geiger counter arrive from somewhere within cone 14. The Geiger counter has no information as to the depth from which the particle comes and cannot even distinguish between particles arriving from different directions within the cone. Thus in principle the prior art Geiger counter gives low resolution one dimensional information.

If the counter is now moved to different positions over the surface of the target then the data from the different positions can be built up into a low resolution two-dimensional image.

One way of increasing the resolution of the Geiger counter is to make it smaller. Then the cone, whilst retaining the same geometry, gives higher resolution data.

The detector takes $(y_t)_{t=1}^{T}$ samples to form a data set, which would typically be a two-dimensional image of the target from a given direction.

Figure 2:
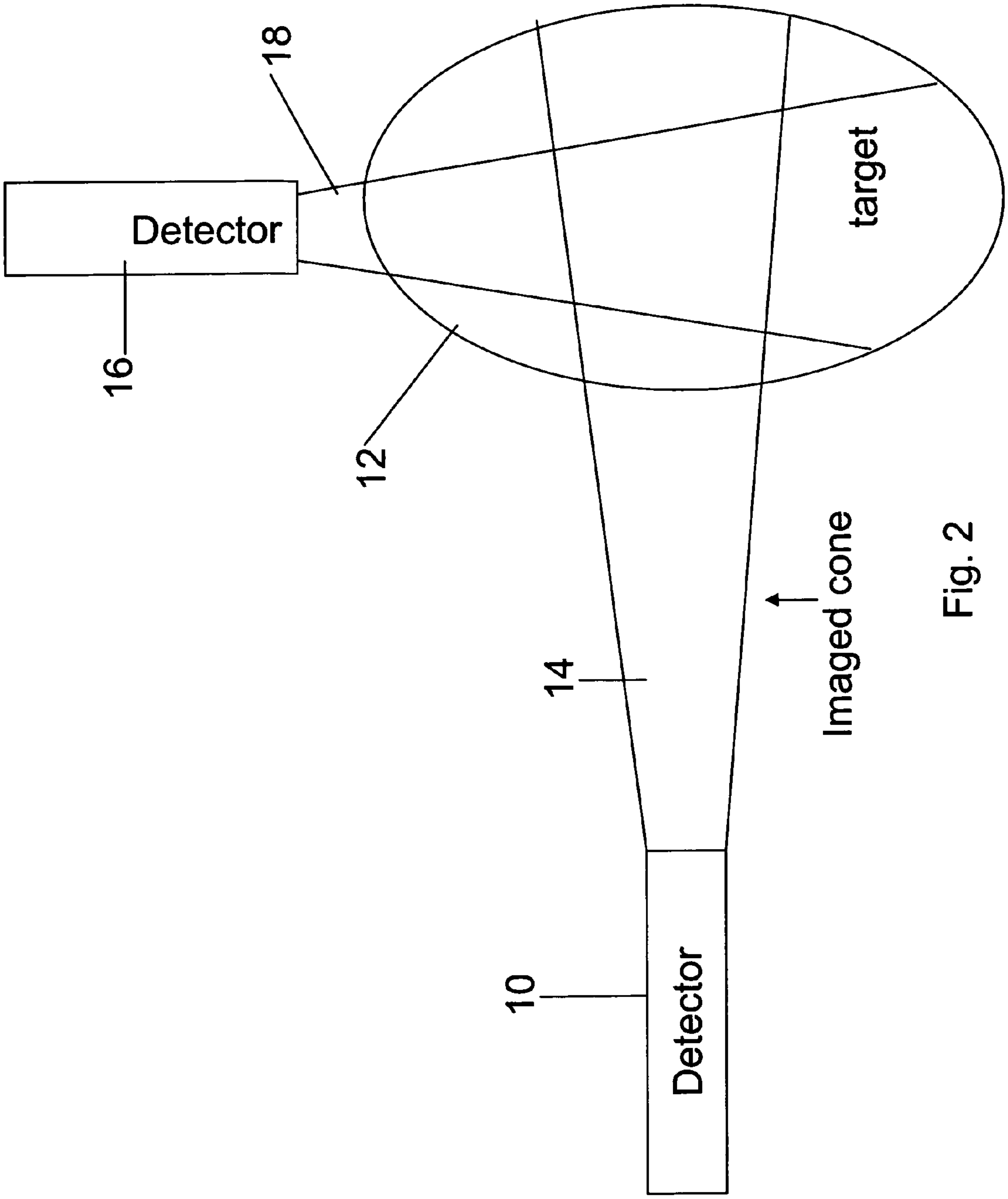
FIG. 2 is a simplified diagram showing two detector positions (not necessarily simultaneously) allowing three-dimensional information to be obtained from a target region.

Reference is now made to FIG. 2, which is a simplified diagram showing how three-dimensional information can be obtained from the target. Parts that are the same as in previous figures are given the same reference numerals and are not referred to again except as necessary for understanding the present embodiment. A second Geiger counter 16 is placed essentially at right angles to the first Geiger counter and obtains a similar kind of image to the first Geiger counter. However, since the two cones overlap, the images produced can be cross-correlated to infer the presence of hot or cold radiation sources in three dimensions.

Figures 3A, 3B, 3C, 3D:
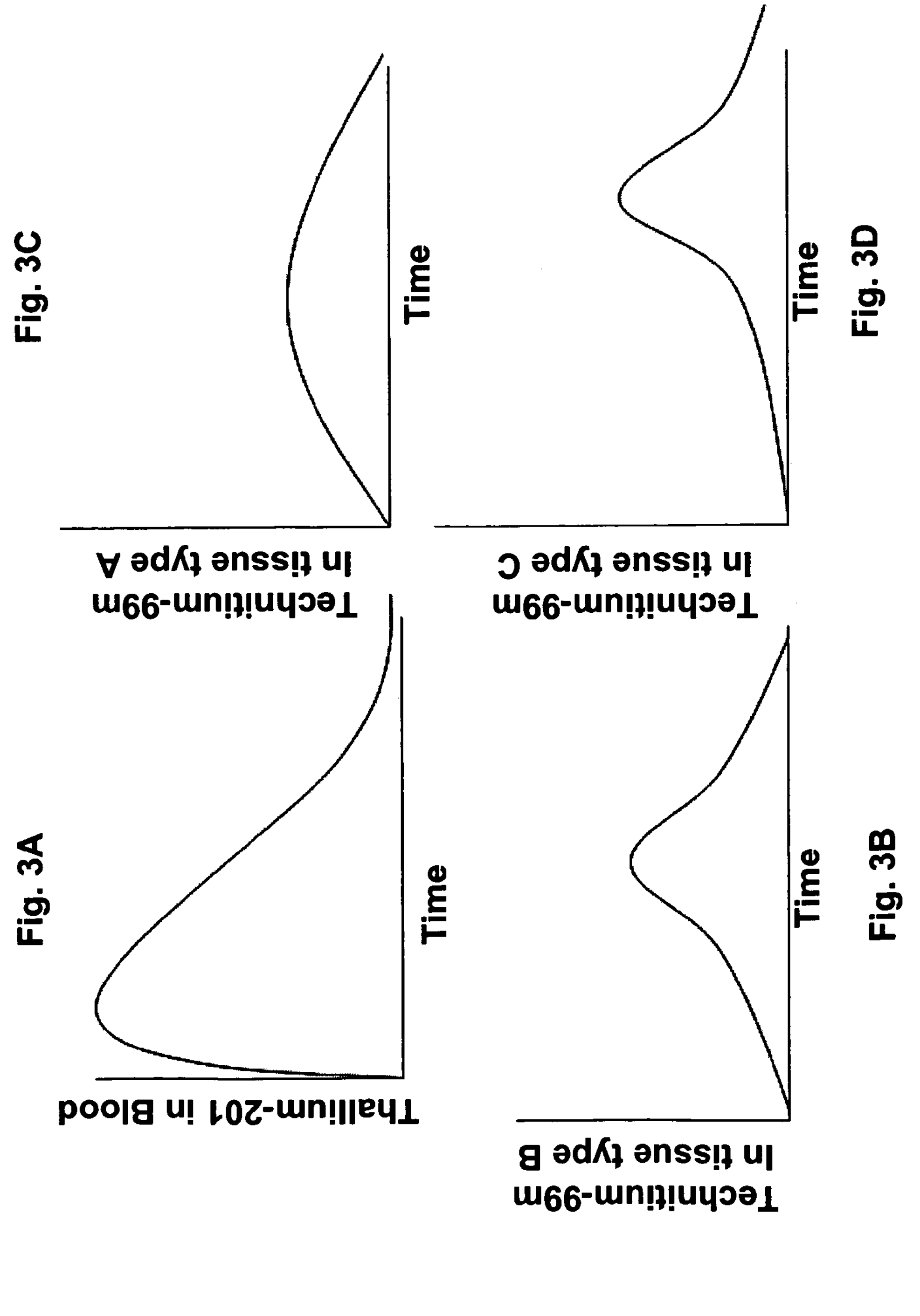
FIGS. 3A–3D show a series of four time absorption characteristics for different radiopharmaceuticals within different tissues.

Reference is now made to FIG. 3, which is a sequence of graphs illustrating the different absorption characteristics for different tissues of a given radioactive marker. Typical markers that may be considered are Thallium-201 and Technitium-99m. FIG. 3*a* indicates a typical absorption characteristic Thallium-201 for blood, Thallium-201 being a particularly good marker for blood. The marker is generally absorbed by the blood fairly rapidly following digestion and then gradually disappears as it is taken up by the various tissues and organs including the kidneys. Marker material from the tissues eventually finds its way back into the blood for excretion. That which is absorbed by the kidneys is excreted directly and not seen again.

FIGS. 3B, 3C and 3D show time absorption characteristics for Technitium-99m for different tissues, and it will be seen that the characteristic is generally curved but peaks at different times for the different tissues.

The principle on which the present embodiments are based is as follows: Considering the graphs in FIG. 3, it will be apparent that a region belonging to a single tissue will behave in a uniform manner as regards signal intensity. That is to say, a given marker will be taken up and then expelled at the same rate over a given tissue, whereas this rate will be different for other tissues. If therefore a series of successive images are taken of the target and the images are analyzed region by region for rates of change of intensity, a particular desired region can be identified by virtue of having rates of change in intensity that fit with a given characteristic. The regions are distinguishable in this way even if the region of interest is heavily overlapped with other regions.

Figure 4:
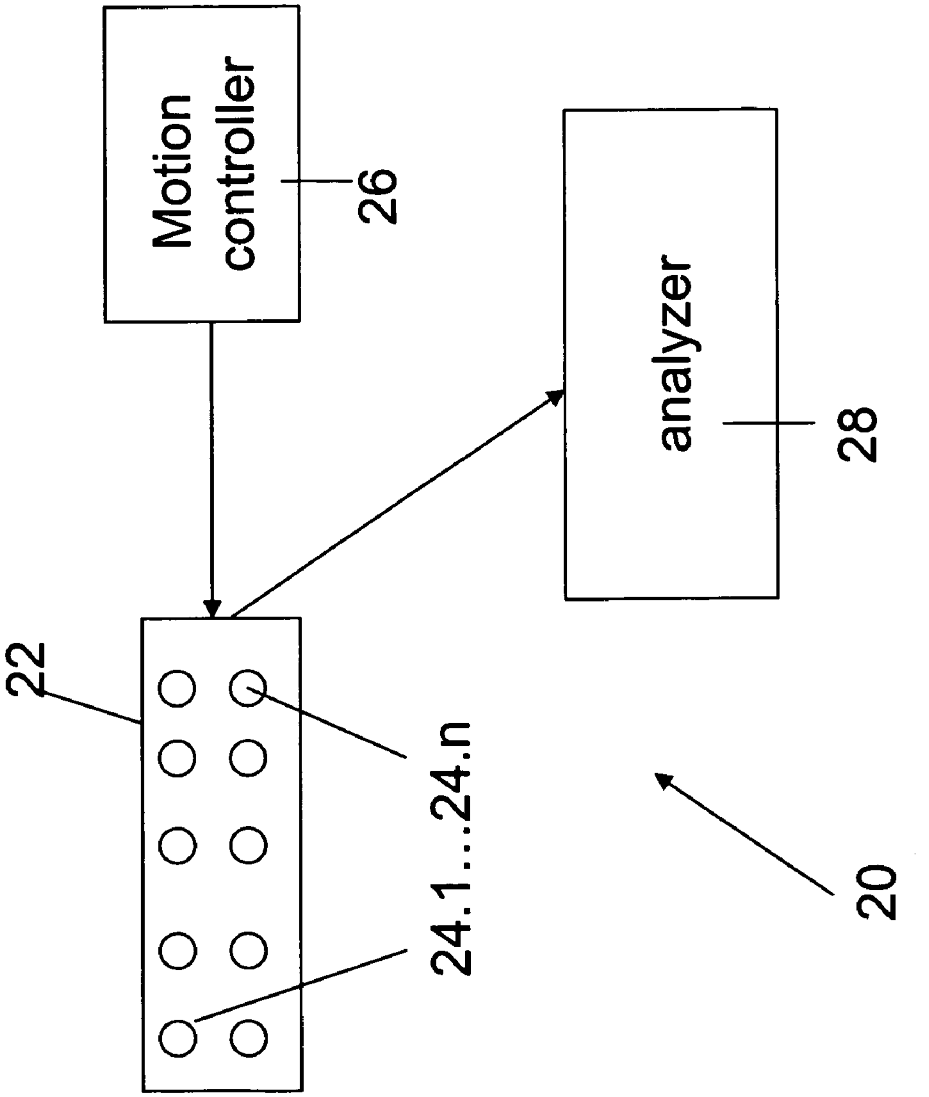
FIG. 4 is a simplified schematic diagram showing a device for driving an imaging head and allowing control of the imaging head by the image analyzer device.

Reference is now made to FIG. 4, which shows apparatus for radiation-based imaging of a non-homogenous target area. Apparatus 20 comprises an imaging unit 22 which itself consists of a series of small Geiger counters 24.1 . . . 24.*n* arranged on an imaging head. The imaging unit is controlled by motion controller 26 to take readings from different locations around the target area. Preferably, the motion of the imaging head is controlled by software via servo-motors. In addition the motions, either of the individual Geiger counters or of groupings of the Geiger counters, is also controlled by software via servo-motors.

In a preferred embodiment, the signals received from the individual Geiger counters are summed to form a three-dimensional image of the target area. The skilled person will appreciate that the system could also be based on a two-dimensional image. In either case, the signals are fed to an image analyzer 28, where the signals are analyzed to form images.

In the preferred embodiments, the image analyzer is able to use the marker take up characteristics to compare successive images and identify regions of particular interest, and then to concentrate imaging resources on those regions. That is to say the image analyzer is in fact able to control further operation of the imager.

Figure 5:
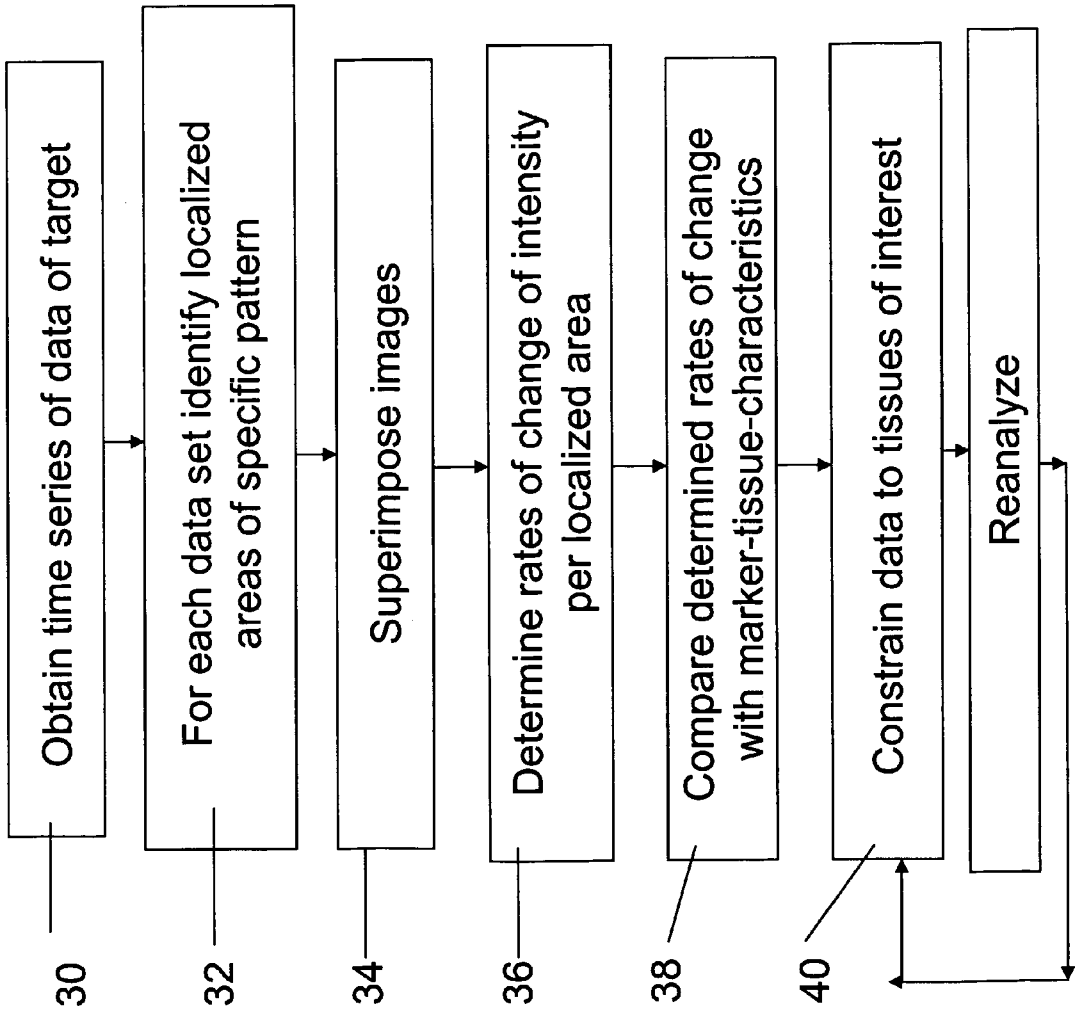
FIG. 5 is a simplified flow chart illustrating the image analysis process carried out by the analyzer in FIG. 4 in the case of a single marker.
Figure 6A:
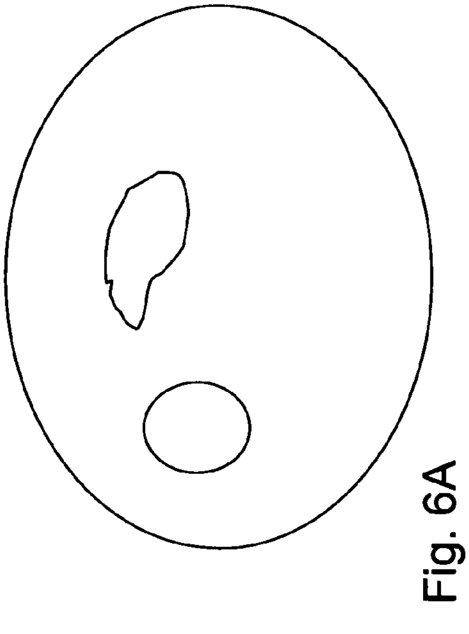
FIGS. 6A–6D illustrate two sets of successive images of the same target area taken using two different markers respectively, according to a preferred embodiment of the present invention.
Figure 6B:
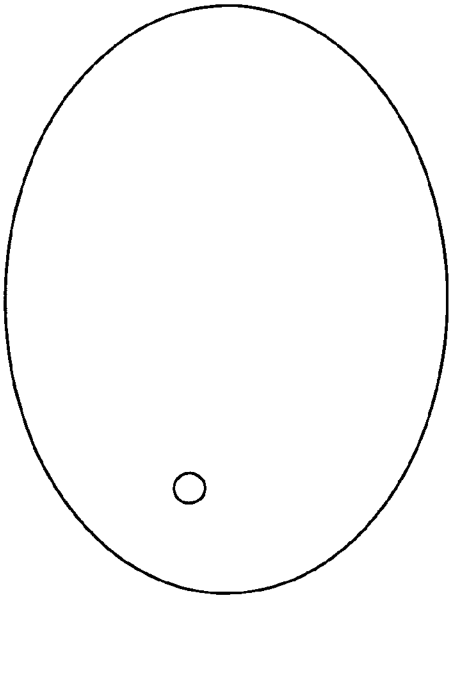
Figure 6C:
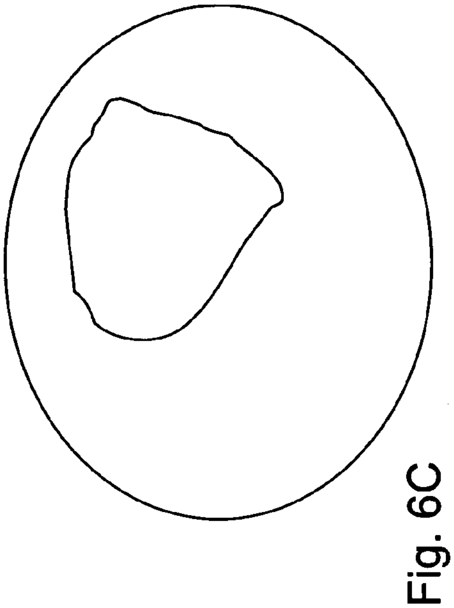
Figure 6D:
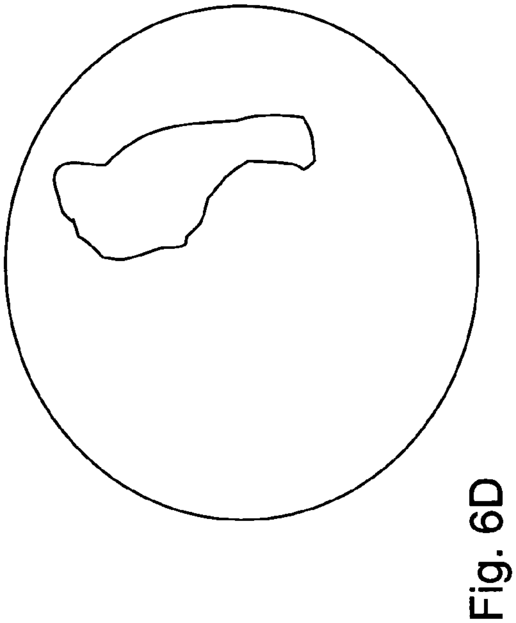

Reference is now made to FIG. 5, which is a simplified flow chart illustrating the image analysis process carried out by analyzer 28 in the case of a single marker. Preferably a series of images of the same views are taken at different times, stage 30, and a three-dimensional overall image of the target is formed for each time. The analyzer then analyzes each of the three-dimensional overall images for local intensities at different locations around the target, stage 32. The local intensities are noted and the same locations on the different images are superimposed in stage 34. From the superpositioning, local rates of change of intensity between the images may be obtained in stage 36. The rates of change are compared with the pre-obtained characteristics for the marker with the different tissues in stage 38, and the data are then constrained to those localities which conform to the desired predetermined characteristics in stage 40. As a result the imaging process can be used to identify and concentrate on localities of interest and data from other localities can be jettisoned. Consequently, the image analysis is able to concentrate its resources on the tissues of interest and a higher resolution final image can be produced.

It will be appreciated that in many cases two types of tissue may be superimposed, of which only one of the tissues is of interest. In this case it is of equal importance both to exclude the one tissue that is not of interest and to include the tissue that is of interest. It may be that the best marker for one tissue may not be the best marker for the other tissue. The system as described with respect to FIGS. 4 and 5 may be adapted to use with two or more markers, as exemplified in FIG. 6. Each marker produces a radioactive particle of different energy level, and therefore the data from the different markers can be collected and summed separately to form different images. Mathematically the different data sets obtained from the different energy level signals may be treated as different dimensions of a multi-dimensional vector. For each of the marker-images the appropriate characteristics are used to identify the tissues of interest, and the results can be cross-checked between the different markers. The different tissues can be mapped and the image analysis can concentrate on the area of interest. As a result the system uses both time and particle energy as separate dimensions in addition to the spatial dimensions in order to characterize or map the tissues.

As a result the image analysis unit is able to produce a final result treating the various tissue regions as separate entities. Furthermore, as the system is aware of the regions as entities it is able to further direct the imaging process to concentrate on the regions of interest.

An example in which regions at least partially overlap is the heart. Generally, scans of the heart are interested in the muscular walls of the heart. Although the chambers of the heart are filled with blood, any signal coming from the blood is in fact noise to this kind of scan. It is therefore advantageous to carry out an imaging process which is able to positively identify signals from the muscular heart walls and at the same time exclude the blood.

Referring now to FIG. 6, and in a preferred embodiment, the patient ingests two markers, Thallium-201 and Technitium-99m. The first of these is an effective blood marker and two successive Thallium-201 images are shown in FIGS. 6*a* and 6*b*, and the second is more effective at marking muscle tissue and two successive images thereof are shown in FIGS. 6*c* and 6*d*. The heart is imaged at intervals chosen both for the characteristic for Thallium-201 in blood and for the characteristic of Technitium-99m in muscle. The result is a series of images for each of the markers. The series for Thallium-201 may be constrained to show the regions of blood quite clearly, and to filter out other regions. In here a blood vessel is shown clearly in 6*a* and more faintly in 6*b* where the Thallium-201 has mostly been flushed out. The series for Technitium-99m, FIGS. 6*c* and 6*d* show muscle wall structures. The first of the two images apparently shows larger structures but in fact all that it is showing is that much Technitium-99m has not yet been absorbed in the muscle. The second image 6*d* may therefore be used to constrain the first image 6*c* to show only the muscle walls regions. The two series of images may then be superimposed to filter out from the Technitium-99m images 6*c* and 6*d* anything that appears strongly in the Thallium-201 images 6*a* and 6*b*. The filtering may additionally remove anything that appears strongly in both images as coming from outside the region.

In the above example, two regions were of respectively positive and negative interest, meaning one for concentrating on and the other for filtering out. It will be appreciated that several regions or several tissue types may be of positive interest or there may be any combination of regions with just one being of positive interest. Alternatively all regions may be of positive interest but importance may be attached to discriminating between the different signals from the different regions.

The system is able to use the mapping to generate an image comprising the different tissue regions as distinct entities. As a consequence of the mapping process, the system is able to be aware electronically of the different regions and thus control both the imaging head and the analysis unit to concentrate their resources on specific regions. The result is greater resolution for the regions of interest.

The preferred embodiments may be used to expand the information obtained from the markers, using either or both of examining the kinetics of the markers over time and using several markers concurrently.

In order to increase the specificity of the test, additional second substances ("secondary substances"), with reactivity and pharmaco-kinetics differing from those of the first substance can be used in order to enhance the differentiation between the different pathologies, as explained above with respect to FIG. 6. The secondary substance, in this case thalium, ideally marks only a subset of the population marked by the primary substance and does so at different rates. Such a difference exists because of different affinity to various cell types and different participation in metabolic reactions of different tissues. The difference is associated with the rate of marking and/or with the location of the marking.

Upon reading the radioactive signals emanating from the voxels stemming from different substances at different time instances, it is possible to build for every voxel a multi dimensional data matrix Sjk whose elements are intensity readings taken at instances K resulting from the interaction of Substance J. Examination of every voxel of tissue in this multidimensional space quantifies the temporal and specific reaction of the tissue to different substances and thus increases the probability of specific detection of different pathologies. Furthermore, standard image processing techniques can be used in order to more accurately define the spatial location of different pathologies.

In addition to the method above, spatial properties that reflect typical relationships between neighboring voxels may also be a criteria and represented as part of the pattern of the tissue type.

Figure 7A:
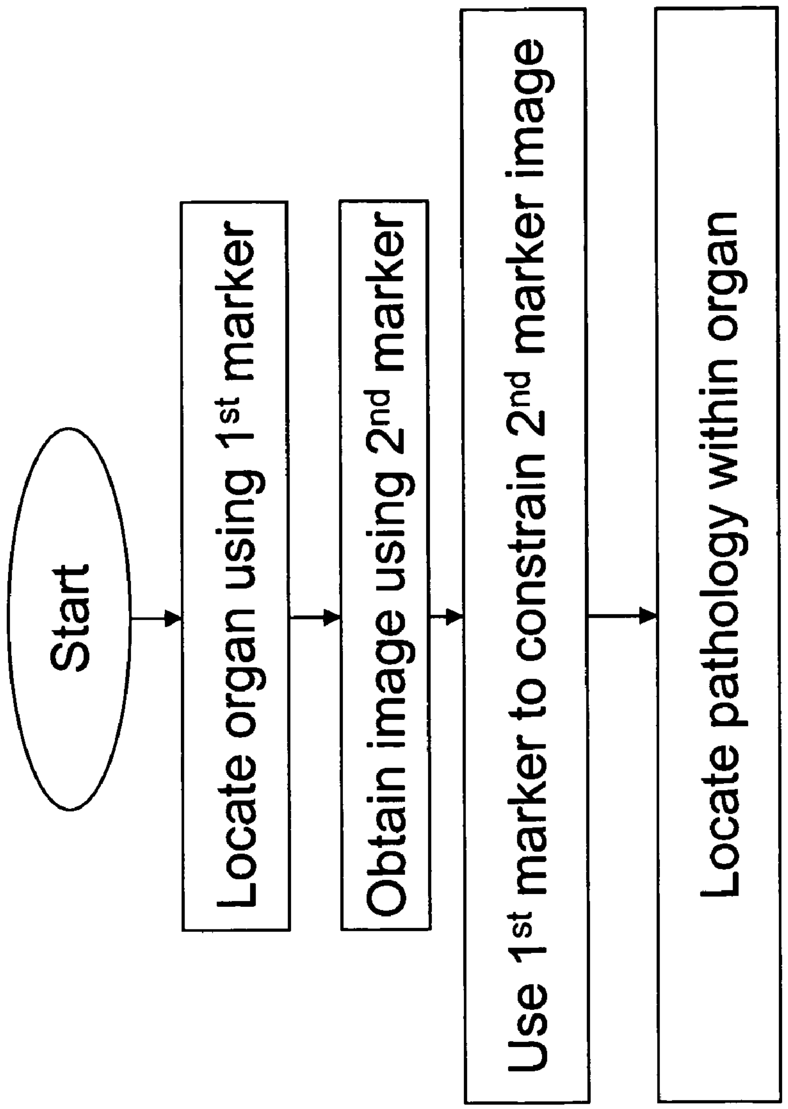
FIG. 7A is a simplified flow chart illustrating a procedure according to a preferred embodiment of the present invention using two or more markers for first of all identifying an organ and then secondly determining the presence or otherwise of a pathology within that organ.
Figure 7B:
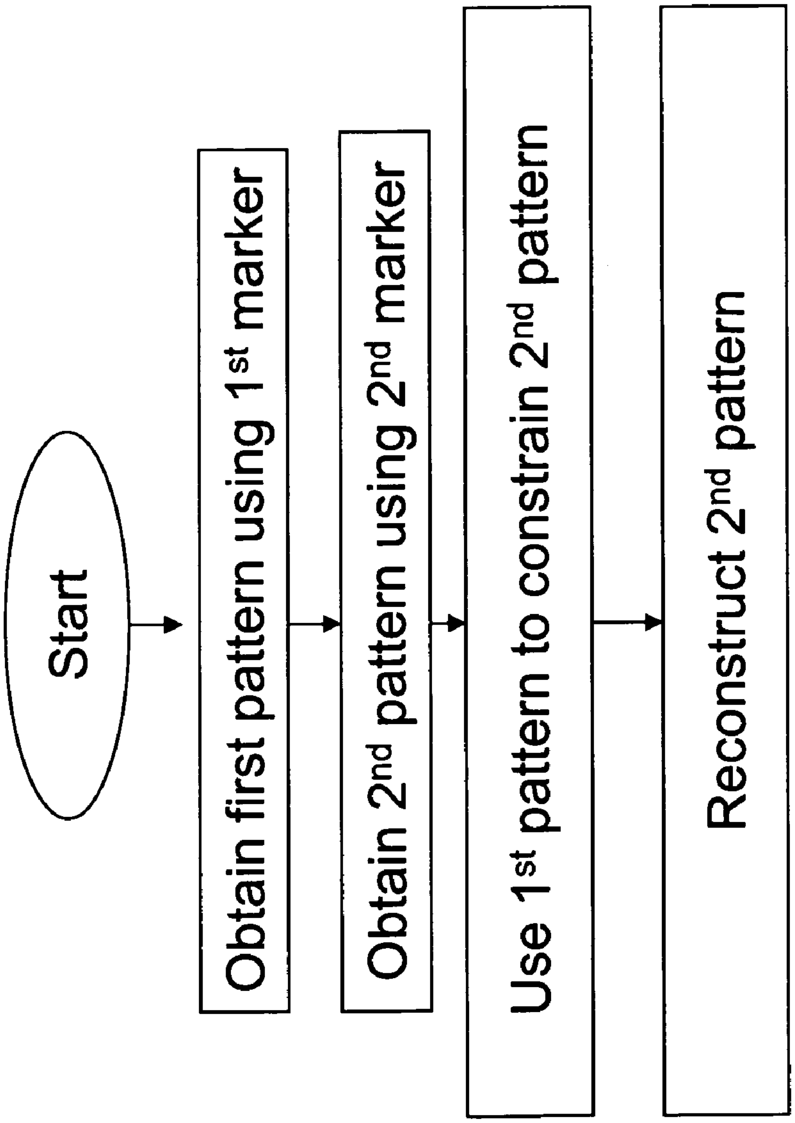
FIG. 7B is a simplified flow chart showing a generalization of FIG. 7A for the general case of two specific patterns.

Reference is now made to FIG. 7, which illustrates an additional statistical approach. In FIG. 7, an automatic algorithm based on expected intensities may be used to determine if the entire organ or region is diseased or non-diseased. Once it is possible to become tissue-aware, as explained above, then it is no longer necessary to carry out such analysis on a voxel-by-voxel basis. Rather the system is able to determine where the organ lies say using a first marker and then a second marker may be imaged using the constraint of the organ location, the second marker being able to locate the presence of the pathology.

Figure 8:
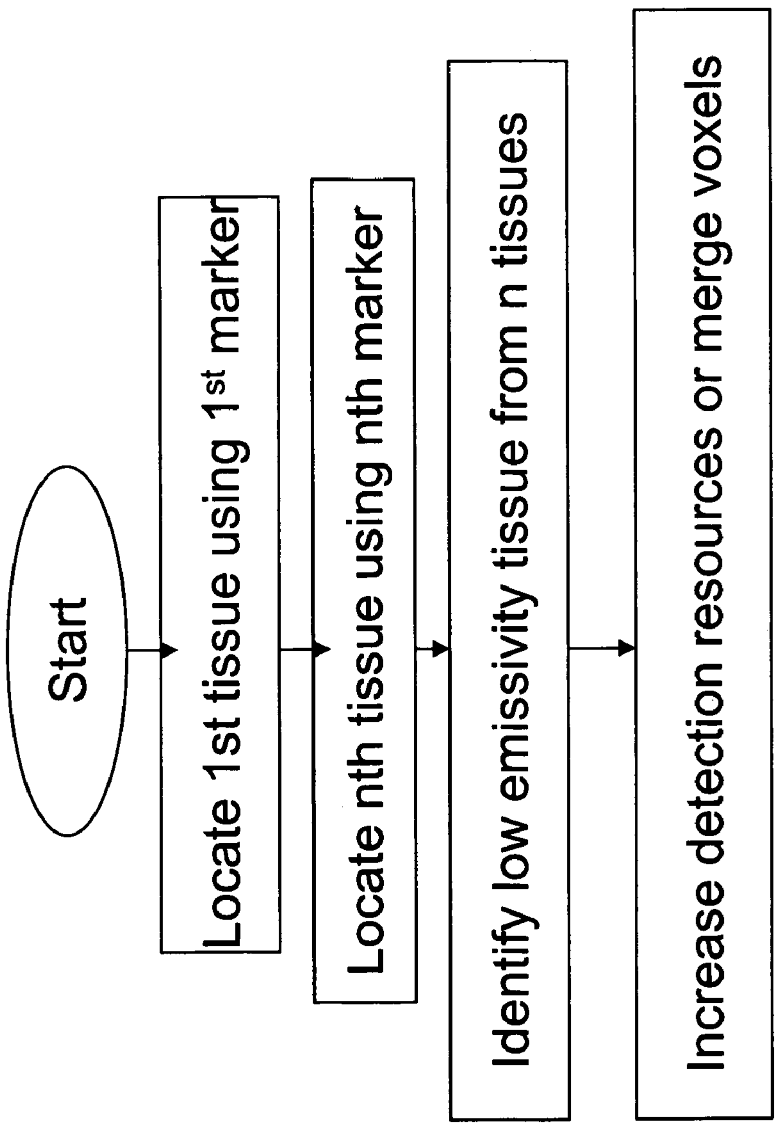
FIG. 8 is a simplified flow chart illustrating a procedure according to a preferred embodiment of the present invention using two or more markers for identifying a region of low emissivity within a target area and using that identification to control imaging resources to better image the identified region.
Figure 9A:
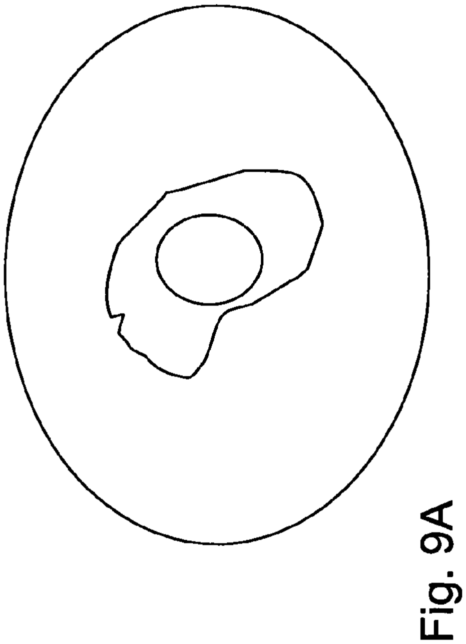
FIGS. 9A–9D illustrate two sets of successive images of the same target area taken using two different markers, in a similar way to that shown in FIG. 6, except that this time the regions of interest are one inside the other.
Figure 9B:
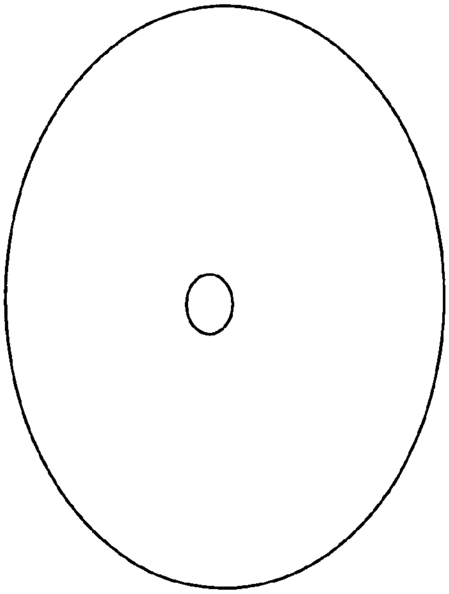
Figure 9C:
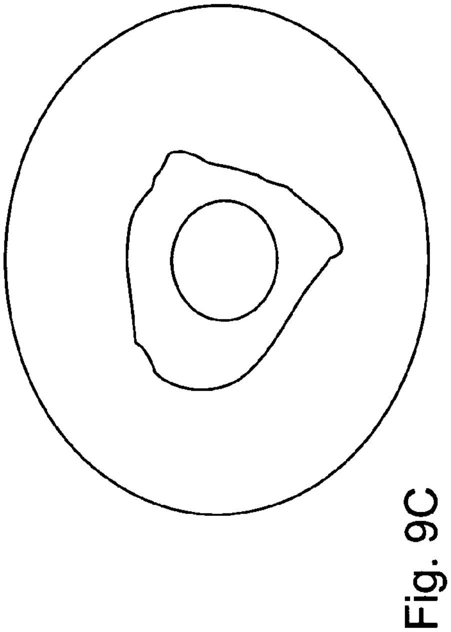
Figure 9D:
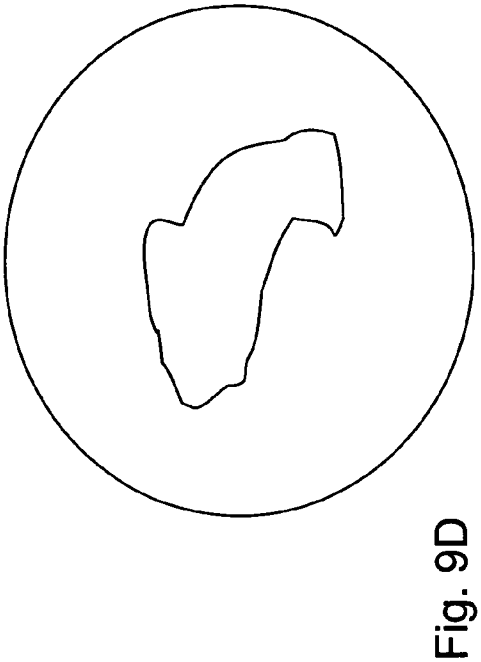

Reference is now made to FIG. 8 which illustrates a method for using the tissue aware properties of the present embodiments in order to tune detection to match tissue or organ emissivities. Generally, any region, no matter how much radiation it produces, can always be imaged sufficiently simply by leaving the measuring device in position for long enough. However, in many cases there may be limited time available. For such cases in which there is limited time for data acquisition, the present embodiments can be used to identify regions that may be expected to produce less emission. The system may then tune imaging resources or resolution onto those tissues according to the number of photons available. Clearly the more photons obtained the more reliable is the data, and therefore a tissue aware system is able to concentrate more detectors on the weaker signaling tissues.

If there are still not enough photons, or there are not enough detectors, then another way of pooling resources is to merge neighboring voxels (or regions). Such a procedure may reduce resolution, but will increase the overall number of photons for that merged region, and thus enable better classification of that region based on a more reliable photon count. Such a compromise enables analysis of the same collected data by ways that would allow high resolution where there are enough photons and lower resolutions where there are less while maintaining reliability of the analysis.

Again the tissue regions may be identified using multiple markers.

The above-described embodiment may lead to controlled sensitivity levels, currently not available with radioimaging.

The concept of using multiple antibodies can be used for therapy purposes, as in the following:

The specificity of a single antibody carrying a drug (or radioactive therapy) determines the chance for non-target tissue to receive the drug, and thus be subject to any toxicity of the drug. In cases where there are several antibodies, each with limited specificity, but with affinity to different 'background' tissue, a combination of antibodies may be used to improve the overall specificity, and thus to reduce overall toxicity and enable higher efficacy of treatment.

For example, if a first antibody (A1) based drug binds to the target N1 folds its affinity to the closest non-target tissue (B1), and a second antibody (A2) with similar drug has target affinity which is N2 folds higher than its closest non-target tissue (B2), then using a merged therapy will enable better target vs. non-target specificity, which is better than N1 and N2 (assuming B1 and B2 are different).

In a more generalized embodiment, the system may include a signal analysis module, including a library of patterns that are typical for every cell type. Each type of cells has one or more patterns associated with it, and the pattern determines how a set of markers injected according to a specific protocol (dosage, time, etc) may be expressed in that cell type. The analysis includes classification of the readings from each voxel based on correlation, or other statistical tools for assessing the most probable tissue classification for each voxel.

Since there may be several cell types for a given disease (e.g. cancer may show in several forms), the algorithm may be optimized to determine the exact tissue type per voxel or region. Alternatively, the algorithm may be optimized to determine the general property of diseased/non-diseased, while taking the specific classification only as a factor in the statistical analysis.

It should be noted that the system may allow for various protocols for administering the markers, where injection of the various markers may be simultaneous, or multiple injections at various times, as various markers have different lifetime in the circulation.

The issue of generating imaging using two or more markers is now considered mathematically.

An intensity distribution I, conventionally defined in terms of radioactive emissions per seconds, is now redefined as a vector of distributions over the volume U, forming our input space. Each dimension of the vector is a different one of the radiopharmaceuticals. The universal set U comprises a set of basic elements u (e.g., pixels in two dimensional spaces, voxels in three dimensional spaces), and I(u) is the intensity in a given basic element $u \in U$. For j radiopharmaceuticals this becomes l(u)(j,t) An inverse (or reconstruction) problem arises when one cannot sample directly from I, but can sample from a given set of views $\Phi$. A projection $\phi \in \Phi$ is defined by the set of probabilities $\{\phi(u): u \in U\}$, where $\phi(u)$ is the probability of detecting a radioactive emission from a voxel u, as defined by viewing parameters, such as the physical and geometrical properties of the detecting unit, as well as the attenuation parameters of the viewed volume U, and the time parameters. A measurement is obtained by choosing a view $\phi \in \Phi$, and then sampling according to the viewing parameters.

For j radiopharmaceuticals or markers and k detectors, the probability of seeing a particle becomes $\phi jk(u)$ In the following analysis, I is the intensity of a radioactive substance, and the viewing parameters include the geometrical properties of a collimated detecting unit and the detecting unit's position and orientation with respect to volume U. The number of radioactive emissions counted by the detecting unit within a time interval is a Poisson distribution, where $\phi(u)$ is the detection probability of a photon emitted from voxel $u \in U$ and the mean of the distribution is the weighted sum $\Sigma u \in U \phi(u) I(u)$.

For the case of the kth detector a measurement $Yk = \Sigma u \in U\ Xt(u)$, where X(U) is a Poisson distribution.

$$X(j,k,t)(u)=I(i,t)(u).\phi(u)jk(u).$$

Where $Y(j,k,t)=\Sigma X(j,k,t)(u)$.

Hence $Y(j,k,t))=\mathrm{Poisson}(Y(j,k,t))$

The projection set is thus defined by a matrix $\Phi$, whose rows are the projections of the chosen views. I is a vector of densities (specified per each element in U), and $\Phi I$ is a vector of respective effective intensity levels for the views in the set. A vector of measurements y is obtained by a random sample from each view (according to the associated Poisson distribution). As discussed above, there are various known reconstruction methods that provide estimators for I given the projections $\Phi$ and the measurements y.

Using the above mathematics the problem is solved (an image created) one of the vectors say once an hour. The rates of change are determined. Simultaneously the problem is solved for another of the vectors at similar time intervals and the rates of change are determined. Then a stage of cross-identification is carried out between the two images, so that wanted tissues as identified by each image minus unwanted tissues identified by each image are concentrated on to form a new image. Cross-identification may be an iterative process.

In the example given above of the imaging of the heart using one blood marker and one muscular tissue marker, the areas identified by the blood marker are subtracted. The areas identified by the muscle marker are added, and those tissues not identified by either are likewise ignored as being signals from outside the target region.

The non-homogenous target area is typically a region of living tissue, generally belonging to a patient. The distinguishable regions within can be different tissues, different organs, a mixture of blood and organ tissue as with the above example of the heart, or tissue regions exhibiting differential pathologies.

It is expected that during the life of this patent many relevant markers, radiological imaging devices and two and three dimensional imaging systems will be developed and the scopes of the corresponding terms herein, are intended to include all such new technologies a priori.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. Apparatus for radiation based imaging of a non-homogenous target area having distinguishable regions therein, the apparatus comprising:

an imaging unit configured to obtain radiation intensity data of at least one radioactive marker, from said target area in spatial dimensions and a time dimension, said at least one radioactive marker having region-dependent, distinguishable, radiation intensity time profiles, and an image four-dimension analysis unit associated with said imaging unit for analyzing said obtained intensity data in said spatial and time dimensions in order to map said distinguishable regions, to a time-characterized mapping, based on said region-dependent, distinguishable, radiation intensity time profiles.

2. Apparatus according to claim 1, wherein said image four dimension analysis unit is configured to constrain image output to a subset of said mapped distinguishable regions.

3. Apparatus according to claim 2, wherein said image four-dimension analysis unit is configured to use said constraining to increase a resolution of said image output.

4. Apparatus according to claim 1, wherein each of said region-dependent, distinguishable, radiation intensity time profiles includes at least one distinguishable attribute, selected from the group consisting of:

a distinguishable time uptake characteristics, a distinguishable time release characteristics, and a combination thereof.

5. Apparatus according to claim 4, wherein said image analysis unit is configured to use said time-characterized mapping to generate an image comprising said distinguishable regions as distinct entities.

6. Apparatus according to claim 4, wherein said image analysis unit is configured to use said time-characterized mapping to generate an image showing only a subset of said distinguishable regions and to exclude at least one other of said distinguishable regions.

7. Apparatus according to claim 4, wherein said distinguishable regions at least partially overlap, said image analysis unit being configured to show radiation due to a subset of said distinguishable regions of said time-characterized mapping, and to exclude radiation from at least one other of said distinguishable regions as noise.

8. Apparatus according to claim 1, wherein at least two radioactive markers are applied to said target area, each of said markers having marker-characterized, region-dependent, distinguishable, radiation intensity time profiles, said image analysis unit being capable of handling at least one additional dimension, and being configured to use distinguishability of the marker-characterized, region-dependent, radiation intensity time profiles between said markers as said additional dimension in order to provide a marker-characterized mapping.

9. Apparatus according to claim 8, wherein said image analysis unit is configured to use said marker-characterized mapping to generate an image comprising said regions as distinct entities.

10. Apparatus according to claim 8, wherein said image analysis unit is configured to use said marker-characterized mapping to generate an image showing only a subset of said distinguishable regions and to exclude at least one other of said distinguishable regions.

11. Apparatus according to claim 8, wherein said distinguishable regions at least partially overlap, said image analysis unit being configured to show radiation due to a subset of said distinguishable regions of said marker-characterized mapping, and to exclude radiation from at least one other of said distinguishable regions of said marker-characterized mapping as noise.

12. Apparatus according to claim 8, wherein one of said radioactive markers is Thallium-201 and another of said radioactive markers is Technetium-99m.

13. Apparatus according to claim 8, wherein said marker-characterized, region-dependent, distinguishable, radiation intensity time profiles are distinguishable by radiation intensity as a function of time.

14. Apparatus according to claim 8, wherein said marker-characterized, region-dependent, distinguishable, radiation intensity time profiles are distinguishable by radiation intensity rate as a function of time.

15. Apparatus according to claim 8, wherein said marker-characterized mapping provides confirmation of said time-characterized mapping.

16. Apparatus according to claim 8, wherein said marker-characterized mapping produces a finer mapping than said time-characterized mapping.

17. Apparatus according to claim 1, wherein said imaging unit comprises at least one directional Geiger counter.

18. Apparatus according to claim 17, wherein said imaging unit comprises a plurality of directional Geiger counters.

19. Apparatus according to claim 17, wherein said imaging unit comprises a controller for directing said Geiger counter to take images from a set of locations optimized to obtain three-dimensional spatial data for a given target area.

20. Apparatus according to claim 1, wherein said non-homogenous target area is a region of living tissue, comprising an inhomogeneity selected from the group consisting of: different tissues, different organs, blood and organ tissue, and tissue regions of differential pathologies.

21. Apparatus according to claim 1, wherein said image analysis unit is configured to ignore image data as being from outside said target area if said image data does not conform to at least one of said region-dependent, distinguishable, radiation intensity time profiles.

22. Apparatus according to claim 1, configured to use said time-characterized mapping to identify at least one distinguishable region of low emissivity, thereby to concentrate imaging resources on said identified region.

23. Apparatus according to claim 22, wherein said imaging is via voxels of said target area and wherein said concentrating imaging resources comprises merging voxels of said identified region.

24. Apparatus according to claim 22, wherein said concentrating resources comprises concentrating resources of said imaging unit on said identified region.

25. Apparatus according to claim 1, wherein said time-characterized mapping comprises a first mapping to identify an organ and a second mapping constrained within said organ.

26. Apparatus according to claim 1, wherein said region-dependent, distinguishable, radiation intensity time profiles are distinguishable by radiation intensity as a function of time.

27. Apparatus according to claim 1, wherein said region-dependent, distinguishable, radiation intensity time profiles are distinguishable by radiation intensity rate as a function of time.

28. A method for constraining image data obtained from a non-homogenous target area having a plurality of distinguishable regions, using at least one radioactive marker, which has region-dependent, distinguishable, radiation intensity time profiles, the method comprising:

obtaining radiation intensity data from said target area in spatial dimensions and at least a time dimension;

analyzing said radiation intensity data using said spatial and time dimensions;

producing a time-characterized mapping, based on said region-dependent, distinguishable, radiation intensity time profiles; and constraining an output to a subset of said distinguishable regions.

29. The method of claim 28, wherein each of said region-dependent, distinguishable, radiation intensity time profiles includes at least one distinguishable attribute, selected from the group consisting of:

a distinguishable time uptake characteristics, a distinguishable time release characteristics, and a combination thereof.

30. The method of claim 28, wherein there are provided at least two radioactive markers, each having marker-characterized, region-dependent, distinguishable, radiation intensity time profiles, and further including:

using distinguishability of the marker-characterized, region-dependent, radiation intensity time profiles between said markers as an additional dimension; and producing a marker-characterized mapping, based on said marker-characterized, region-dependent, distinguishable, radiation intensity time profiles, to supplement said time-characterized mapping.

31. The method according to claim 30, wherein said marker-characterized mapping provides confirmation of said time-characterized mapping.

32. The method according to claim 30, wherein said marker-characterized mapping produces a finer mapping than said time-characterized mapping.

33. The method according to claim 30, wherein one of said radioactive markers is Thallium-201 and another of said radioactive markers is Technetium-99m.

34. The method of claim 28, wherein said time-characterized mapping identifies at least one region of low emissivity, the method further comprising concentrating imaging resources on said identified region.

35. The method of claim 34, wherein said imaging is via voxels of said target area and wherein said concentrating imaging resources comprises merging voxels of said identified region.

36. The method of claim 34, wherein said concentrating resources comprises concentrating resources of said imaging unit on said identified region.

37. The method of claim 28, wherein said time-characterized mapping comprises a first mapping to identify an organ and a second mapping constrained within said organ.

38. The method according to claim 28, wherein said region-dependent, distinguishable, radiation intensity time profiles are distinguishable by radiation intensity as a function of time.

39. The method according to claim 28, wherein said region-dependent, distinguishable, radiation intensity time profiles are distinguishable by radiation intensity rate as a function of time.

40. The method according to claim 28, wherein said non-homogenous target area is a region of living tissue, comprising an inhomogeneity selected from the group consisting of: different tissues, different organs, blood and organ tissue, and tissue regions of differential pathologies.

41. Apparatus for radiation based imaging of a non-homogenous target area having distinguishable regions therein, the apparatus comprising:

an imaging unit configured to obtain radiation intensity data of at least one radioactive marker, from said target area in spatial dimensions and a time dimension, said at least one radioactive marker having region-dependent, distinguishable, radiation intensity time profiles, and an image analysis unit associated with said imaging unit for analyzing said obtained intensity data in said spatial and time dimensions in order to map said distinguishable regions, to a time-characterized mapping, based on said region-dependent, distinguishable, radiation intensity time profiles, and using said time-characterized mapping to control use of imaging resources.

42. A method for mapping image data obtained from a non-homogenous target area having a plurality of distinguishable regions, using at least one radioactive marker, which has region-dependent, distinguishable, radiation intensity time profiles, the method comprising:

obtaining radiation intensity data from said target area in spatial dimensions and a time dimension;

analyzing said radiation intensity data using said spatial and time dimensions; and producing a time-characterized mapping, based on said region-dependent, distinguishable, radiation intensity time profiles.

43. The method according to claim 42, wherein each of said region-dependent, distinguishable, radiation intensity time profiles includes at least one distinguishable attribute, selected from the group consisting of:

a distinguishable time uptake characteristics, a distinguishable time release characteristics, and a combination thereof.

44. The method of claim 42, wherein there are provided at least two radioactive markers, each having respectively a marker-characterized, region-dependent, distinguishable, radiation intensity time profile, and further including:

using distinguishability of the marker-characterized, region-dependent, radiation intensity time profiles between said markers as an additional dimension; and producing a marker-characterized mapping, based on said marker-characterized, region-dependent, distinguishable, radiation intensity time profiles.

45. The method according to claim 44, wherein said marker-characterized mapping provides confirmation of said time-characterized mapping.

46. The method according to claim 44, wherein said marker-characterized mapping produces a finer mapping than said time-characterized mapping.

47. The method according to claim 44, wherein one of said radioactive markers is Thallium-201 and another of said radioactive markers is Technetium-99m.

48. The method according to claim 44, wherein said marker-characterized, region-dependent, distinguishable, radiation intensity time profiles are distinguishable by radiation intensity as a function of time.

49. The method according to claim 44, wherein said marker-characterized, region-dependent, distinguishable, radiation intensity time profiles are distinguishable by radiation intensity rate as a function of time.

50. The method according to claim 42, wherein said region-dependent, distinguishable, radiation intensity time profiles are distinguishable by radiation intensity as a function of time.

51. The method according to claim 42, wherein said region-dependent, distinguishable, radiation intensity time profiles are distinguishable by radiation intensity rate as a function of time.

52. The method according to claim 42, wherein said non-homogenous target area is a region of living tissue, comprising an inhomogeneity selected from the group consisting of: different tissues, different organs, blood and organ tissue, and tissue regions of differential pathologies.

* * * * *